US00PP32748P2

(12) United States Plant Patent
Berry

(10) Patent No.: US PP32,748 P2
(45) Date of Patent: Jan. 12, 2021

(54) ***HIBISCUS* PLANT NAMED 'JBG BH-06'**

(50) Latin Name: *Hibiscus rosa-sinensis*
Varietal Denomination: JBG BH-06

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 16/602,833

(22) Filed: Dec. 9, 2019

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — The Webb Law Firm

(57) ABSTRACT

A new and distinct *Hibiscus* plant having bright red-orange colored flowers with a white colored eye/throat zone and eye zone extensions that last for several days on the plant.

2 Drawing Sheets

Botanical classification: *Hibiscus rosa-sinensis.*
Varietal denomination: 'JBG BH-06'.

BACKGROUND OF THE INVENTION

The present invention comprises a new and distinct *Hibiscus* plant having the varietal name 'JBG BH-06'. The new variety is the result of a planned breeding program with the purposes of developing *Hibiscus rosa-sinensis* plants that exhibit pathogen resistance, multi-day flowers with unique coloration, and possess desirable production traits. 'JBG BH-06' is the result of a cross conducted in Grand Saline, Tex. between *Hibiscus rosa-sinensis* varieties 'JBG MH-20' (female parent, unpatented) and 'JBG AH-19' (male parent, unpatented). The new variety was selected in December of 2016 in Grand Saline, Tex. and the first asexual reproduction of the new variety was conducted by semi-hardwood cuttings in February of 2017 in Grand Saline, Tex. 'JBG BH-06' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG BH-06' is similar to its female parent in having a red toned main flower color, high level of disease resistance, high flower count, and having flowers that stay open on the plant for three days. However, 'JBG BH-06' differs from its female parent in that the new variety has a white colored eye/throat zone and eye zone extensions, while 'JBG MH-20' has a dark colored eye zone. 'JBG BH-06' is similar to its male parent in having a low pollen count, upright growth habit, and having flowers that stay open on the plant for three days. However, 'JBG BH-06' differs from its male parent in that 'JBG AH-19' has a yellow toned main flower color with peach colored petal margins.

When 'JBG BH-06' is compared to *Hibiscus rosa-sinensis* variety 'JBG 14015' (U.S. Plant Pat. No. 30,636), both varieties exhibit long eye zone extensions, resistance to bacterial leaf spot (*Pseudomonas* spp.), and multi-day, red toned flowers. However, the flowers of 'JBG BH-06' exhibit a white colored eye/throat zone and eye zone extensions, while the eye/throat zone of the flowers of 'JBG 14015' is deep red in color. Further, JBG BH-06' exhibits a less ruffled flower petal margin and less pronounced crenate leaf margin than 'JBG 14015'.

The following traits distinguish 'JBG BH-06' as a new and distinct cultivar from other *Hibiscus* varieties known to the breeder:

1. Upright habit with a high bud count;
2. Bright red-orange colored flowers with a white colored eye/throat zone and eye zone extensions;
3. High degree of disease resistance, particularly to bacterial leaf spot (*Pseudomonas* spp.);
4. Multi-day flowers; and
5. High growth rate.

DESCRIPTION OF THE DRAWINGS

The accompanying photographic images illustrate the new variety at approximately six months of age, with the colors being as nearly true as is possible with color illustrations of this type.

DESCRIPTION OF THE PLANT

Figure 1:
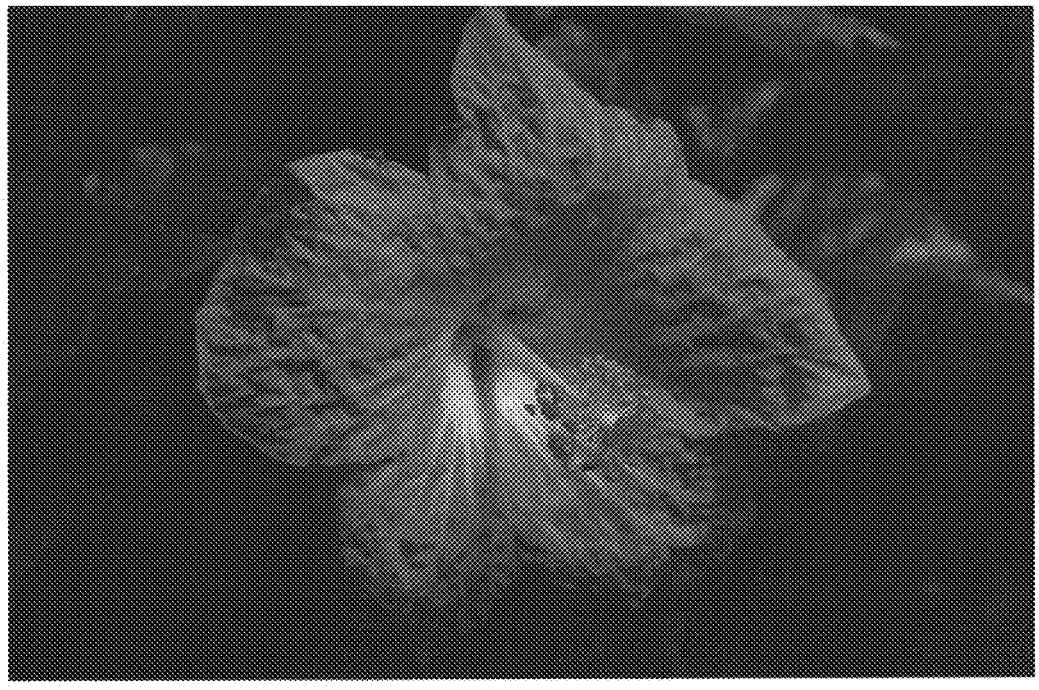
FIG. 1 illustrates a close-up view of a flower of the new variety.
Figure 2:
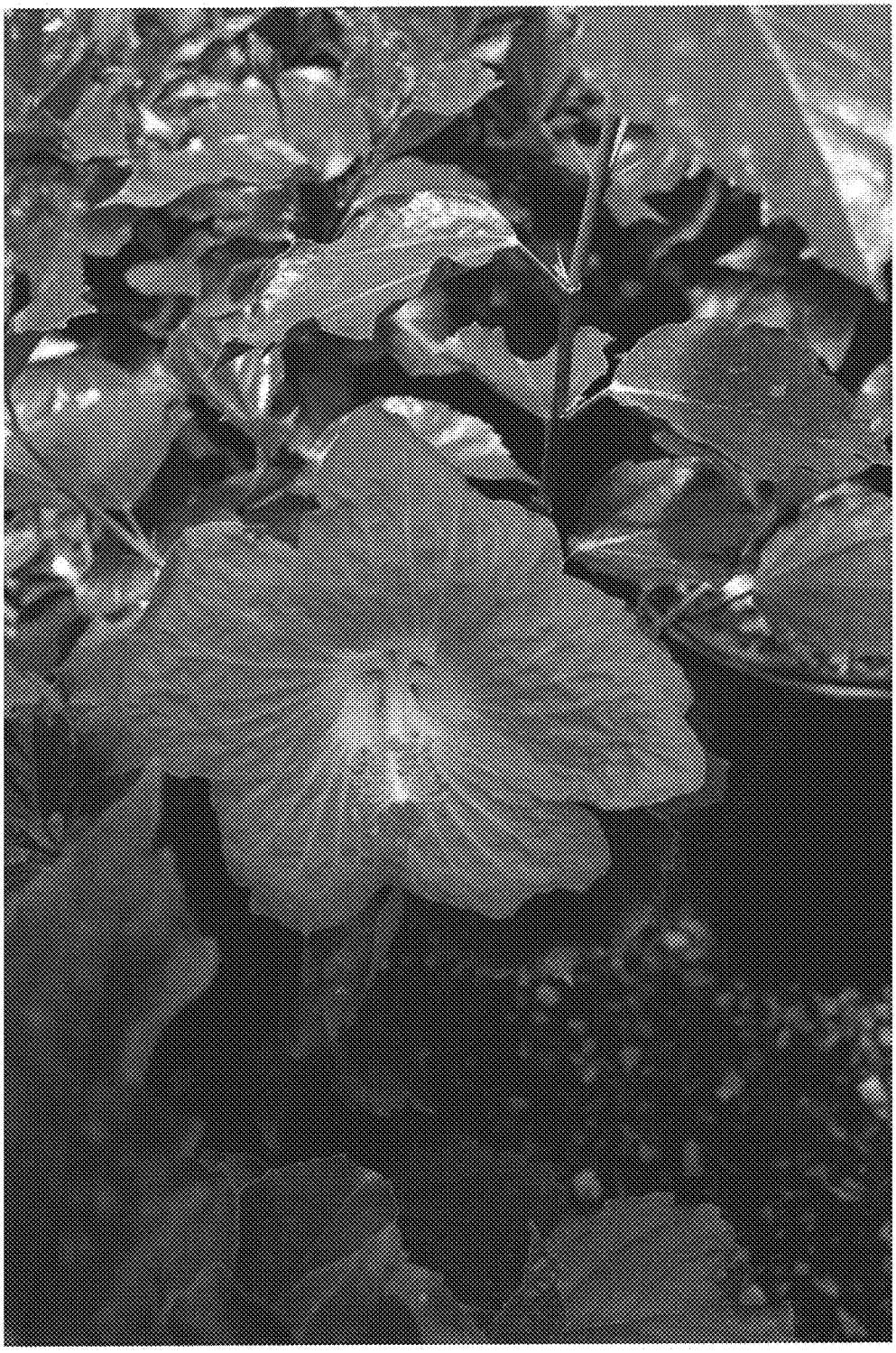
FIG. 2 illustrates a close-up view of plant of the new variety.

The following detailed description sets forth the characteristics of the new variety. The plants were grown in a greenhouse heated to a minimum of 16° C. and covered with 33% black shade cloth. The color readings and measurements were taken in the fall in Grand Saline, Tex. under natural light on approximately eight months old plants that were grown in 24.0 cm diameter containers. Color references are primarily to The 1995 R.H.S. Colour Chart of The Royal Horticultural Society of London, 3rd Edition, except where general color terms are used.

PLANT

Time to initiate roots: About 45 days at an average of 24° C.
Time to develop roots: About 52 days at an average of 24° C.
Time to produce a finished flowering plant from a rooted cutting: About 32 weeks in a 24.0 cm diameter container.
Specific disease/pest resistance: Resistance to bacterial leaf spot (*Pseudomonas* spp.).
Heat/cold tolerance: Nothing unusual noted to date.
Drought tolerance: Nothing unusual noted to date.
Plant:
*Type*.—Tropical, ornamental shrub.
*Habit*.—Upright.
*Height*.—75.0 cm.
*Spread*.—60.0 cm.
*Vigor*.—Moderate to strong.
*Rooting*.—Fibrous and well branched.
Stem:
*Number per plant*.—17-25.
*Length*.—Ranging from 5.0-32.0 cm.
*Width*.—0.4-4.0 mm.
*Texture*.—Immature: Smooth to scabridulous. Mature: Vertically ridged.
*Strength*.—Moderate.
*Branch number*.—Approximately 35.
*Internode length*.—1.0-4.5 cm.
*Color*.—Immature: 144A. Mature: 199D.
*Stipules*.—Number per node: 2. Shape: Spinose. Length: 5.0-10.0 mm. Width: 1.0 mm. Surface texture: Smooth to slightly flocculent. Apex: Acute. Base: Linear. Margin: Smooth to fimbriate. Color: 144A.
Foliage:
*Arrangement*.—Alternate; simple.
*Size of leaf: Length:* 5.0-9.0 cm. Width: 4.0-7.0 cm.
*Shape of leaf* (*generally*).—Ovate.
*Shape of apex*.—Acute to subacute.
*Shape of base*.—Rounded.
*Texture* (*both surfaces*).—Scabridulous.
*Margin type*.—Crenate.
*Blade lobing*.—Absent.
*Margin variegation*.—Absent.
*Color*.—Young leaves: Upper surface: 137B. Lower surface: 137C. Mature leaves: Upper surface: 137A. Lower surface: 137C.
*Veins*.—Venation type: Pinnate. Color: Upper surface: 137A. Lower surface: 137C.
*Petiole*.—Length: 1.5-3.5 cm. Diameter: 1.0-2.0 mm. Texture: Mostly smooth with a scabrous top surface. Color: 143A.

FLOWERS

Buds (described approximately 1 day before flowering):
*Shape*.—Attenuate.
*Diameter*.—2.0 cm.
*Length*.—6.5 cm.
*Color*.—184A.
Natural flowering season: From spring through fall in Grand Saline, Tex. under outdoor conditions. Semperflorous in a heated greenhouse.
Flower type and habit: Single, with overlapping petals.
Fragrance: None observed.
Flowers:
*Number per stem*.—1.
*Overall depth*.—8.0 cm.
*Overall diameter*.—14.0 cm.
*Shape*.—Rotate; regular.
*Lastingness*.—3 days on the plant.
*Petals*.—Number: 5. Arrangement: Simple. Length: 9.0 cm. Width: Apex: 5.5 cm. Base: 1.0 cm. Shape: Ovate. Apex: Obtuse. Base: Acute. Margin: Entire. Texture/appearance: Upper surface: Smooth, with slight ruffling at the apex. Lower surface: Setulose. Color: When opening and fully opened: Upper surface: 44A at the apex through the center and 155C at the eye/throat zone, with a 7.0 mm eye zone extension of 155C. Lower surface: Generally 47A, with 155B at the base. Attitude: Outermost petals are horizontal.
*Calyx*.—Form: Fused. Overall length: 2.5 cm. Overall diameter: 3.0 cm. Sepals/calyx lobes: Number: 5. Shape: Lanceolate. Apex: Acute. Margin: Entire. Texture: Scabridulous. Color: Outer surface: 144B. Inner surface: 144C.
*Epicalyx*.—Length: 1.3 cm. Width: 3.0 mm. Texture: Scabridulous. Color: 144A.
*Bracts*.—Not present (see epicalyx).
*Peduncle*.—Length: 3.0 cm. Diameter: 2.0 mm. Strength: Strong. Angle: Acute. Texture: Scabridulous. Color: 144C.
Reproductive organs:
*Gynoecium*.—Pistils: Number: 1. Length: 7.0 cm. Stigma: Number: 5. Shape: Round. Length: 3.0 mm. Diameter: 2.0 mm. Color: 42A. Style: Length: 5.5 cm. Width: 3.0 mm at the apex; 5.0 mm at the base. Color: 155A. Ovary: Shape: Ovate. Length: 5.0 mm. Width: 4.0 mm. Color: 155D.
*Androecium*.—Stamens: Number: 84. Position: Just below the stigma on the style. Anther: Shape: U-shaped. Diameter: 1.0 mm. Color: 183A. Filament: Length: 6.0 mm. Width: 1.0 mm. Color: 36B. Pollen: Color: 13B. Amount (generally): Low.

SEEDS

Seeds:
*Number*.—From 0 to 20.
*Color*.—200B.
*Length*.—4.0 mm.
*Width*.—4.0 mm.

I claim:

1. A new and distinct variety of *Hibiscus* plant, as is herein illustrated and described.

* * * * *